United States Patent [19]
Gebeyehu et al.

[11] Patent Number: 5,334,761
[45] Date of Patent: Aug. 2, 1994

[54] CATIONIC LIPIDS

[75] Inventors: Gulilat Gebeyehu, Silver Spring; Joel A. Jessee, Mt. Airey; Valentina C. Ciccarone, Gaithersburg; Pamela Hawley-Nelson, Silver Spring, all of Md.; Anna Chytil, Nashville, Tenn.

[73] Assignee: Life Technologies, Inc., Gaithersburg, Md.

[21] Appl. No.: 937,508

[22] Filed: Aug. 28, 1992

[51] Int. Cl.$^5$ ............................................. C07C 233/36
[52] U.S. Cl. ..................... 564/197; 554/105; 554/106; 554/107; 560/222; 560/251; 564/292; 564/504; 206/569
[58] Field of Search ............... 260/404; 560/222, 251; 564/292, 197, 504; 554/105, 106, 107; 206/569

[56] References Cited

U.S. PATENT DOCUMENTS 4,897,355  1/1990  Eppstein et al. ............... 435/240.2
5,889,953  12/1989  Inoue et al. ...................... 564/293

FOREIGN PATENT DOCUMENTS 0394111  10/1990  European Pat. Off. .

OTHER PUBLICATIONS

Felgner et al. (1987) Proc. Natl. Acad. Sci. USA 84:7413–7417.
Zhou et al. (1991) Biochim. Biophys. Acta 1065:8–14.

Primary Examiner—Richard L. Raymond
Attorney, Agent, or Firm—Greenlee and Winner

[57] ABSTRACT

The present invention discloses cationic lipids useful for making lipid aggregates for delivery of macromolecules and other compounds into cells. They are especially useful for the DNA-dependent transformation of cells. Also disclosed are lipids useful both for the delivery of macromolecules and also useful as intermediates for making other such lipids.

18 Claims, No Drawings

CATIONIC LIPIDS

FIELD OF THE INVENTION

Cationic lipid compounds are disclosed, having utility in lipid aggregates for delivery of macromolecules and other compounds into cells.

BACKGROUND OF THE INVENTION

Lipid aggregates such as liposomes have been found to be useful as agents for delivery to introduce macromolecules, such as DNA, RNA, protein, and small chemical compounds such as pharmaceuticals, to cells. In particular, lipid aggregates comprising cationic lipid components have been shown to be especially effective for delivering anionic molecules to cells. In part, the effectiveness of cationic lipids is thought to result from enhanced affinity for cells, many of which bear a net negative charge. Also in part, the net positive charge on lipid aggregates comprising a cationic lipid enables the aggregate to bind polyanions, such as nucleic acids. Lipid aggregates containing DNA are known to be effective agents for efficient transfection of target cells.

The structure of various types of lipid aggregates varies, depending on composition and method of forming the aggregate. Such aggregates include liposomes, unilamellar vesicles, multilameller vesicles, micelles and the like, having particle sizes in the nanometer to micrometer range. Methods of making lipid aggregates are by now well-known in the art. The main drawback to use of conventional phospholipid-containing liposomes for delivery is that the material to be delivered must be encapsulated and the liposome composition has a net negative charge which is not attracted to the negatively charged cell surface. By combining cationic lipid compounds with a phospholipid, positively charged vesicles and other types of lipid aggregates can bind DNA, which is negatively charged, can be taken up by target cells, and can transfect target cells. (Felgner, P. L. et al. (1987) Proc. Natl. Acad. Sci. USA 84:7413-7417; Eppstein, D. et al., U.S. Pat. No. 4,897,355.)

A well-known cationic lipid disclosed in the prior art is N-[1-(2,3-dioleoyloxy)propyl]-N,N,N-trimethylammonium chloride (DOTMA). The structure of DOTMA is:

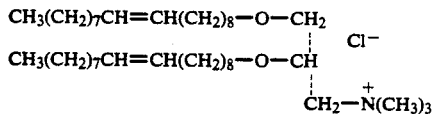

DOTMA by itself or in 1:1 combination with dioleoylphosphatidylethanolamine (DOPE) is formulated into liposomes using standard techniques. Felgner, et al. supra demonstrated that such liposomes provided efficient delivery of nucleic acids to some types of cells. A DOTMA:DOPE (1:1) formulation is sold under the tradename LIPOFECTIN (Gibco/BRL: Life Technologies, Inc., Gaithersburg, Md.). Another commercially available cationic lipid is 1,2-bis(oleoyloxy)-3-3-(trimethylammonia) propane (DOTAP), which differs from DOTMA only in that the oleoyl moieties are linked via ester, rather than ether bonds to the propylamine. DOTAP is believed to be more readily degraded by target cells. A related group of prior art compounds differ from DOTMA and DOTAP in that one of the methyl groups of the trimethylammonium group is replaced by a hydroxyethyl group. Compounds of this type are similar to the Rosenthal Inhibitor (RI) of phospholipase A (Rosenthal, A. F. and Geyer, R. P. (1960) J. Biol. Chem. 235:2202-2206) which has stearoyl esters linked to the propylamine core. The dioleoyl analogs of RI are commonly abbreviated as DORI-ether and DORI-ester, depending on the linkage of the fatty acid moieties to the propylamine core. The hydroxy group can be used as a site for further functionalization, for example by esterification to carboxyspermine.

Another class of prior art compounds has been disclosed by Behr et al. (1989) Proc. Natl. Acad. Sci. USA 86:6982-6986; EPO publication 0 394 111 (Oct. 24, 1990), in which carboxyspermine has been conjugated to two types of lipids. The structures of 5-carboxyspermylglycine dioctadecylamide (DOGS) is:

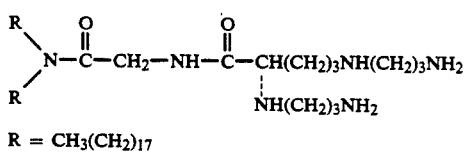

The structure of dipalmitoylphosphatidylethanolamine 5-carboxyspermylamide (DPPES) is:

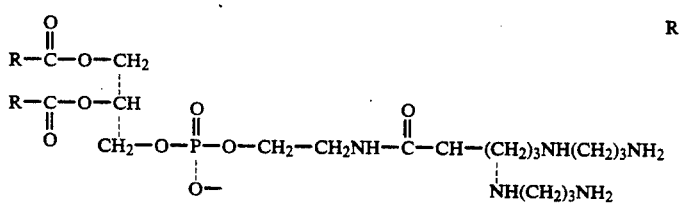

Both DOGS and DPPES have been used to coat plasmids, forming a lipid aggregate complex that provides efficient transfection. The compounds are claimed to be more efficient and less toxic than DOTMA for transfection of some cell lines. DOGS is available commercially as TRANSFECTAM ™ (Promega, Madison, Wis.).

A cationic cholesterol derivative (DC-Chol) has been synthesized and formulated into liposomes in combination with DOPE. (Gao, X. and Huang, L. (1991) Biochim. Biophys. Res. Comm. 179:280-285) The compound's structure is

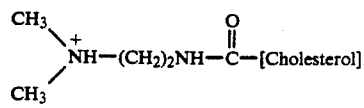

Liposomes formulated with DC-Chol are said to provide more efficient transfection and lower toxicity than DOTMA-containing liposomes for some cell lines.

Lipopolylysine, formed by conjugating polylysine to DOPE, has been reported to be especially effective for transfection in the presence of serum, a condition likely to be encountered in vivo (Zhou, X. et al. (1991) Biochim. Biophys. Acta 1065:8-14).

Despite advances in the field, a need remains for a variety of improved cationic lipid compounds. In particular, no single cationic lipid to date has been found to work well with all cell types. Since different cell types differ from one another in membrane composition, it is not surprising that different compositions and types of lipid aggregate are effective for different cell types, either for their ability to contact and fuse with target cell membranes, or for aspects of the transfer process itself. At present these processes are not well understood, consequently the design of effective cationic lipids is largely empirical. Besides content and transfer, other factors are of importance, for example, ability to form lipid aggregates suited to the intended purpose, toxicity to the target cell, stability as a carrier for the compound to be delivered, and ability to function in an in vivo environment. In addition, lipid aggregates can be improved by broadening the range of substances which can be delivered to cells. The cationic lipid compounds of the present invention have improved function with respect to several of the foregoing attributes.

SUMMARY OF THE INVENTION

The present invention provides novel cationic lipids according to the general formula:

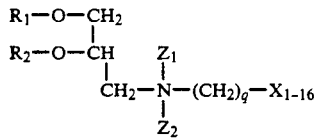

wherein $R_1$ and $R_2$ separately or together are $C_{1-23}$ alkyl or or

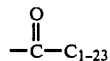

alkyl or alkenyl,
q is 1 to 6,
$Z_1$ and $Z_2$ separately or together are H or unbranched alkyl $C_{1-6}$
$X_1$ is —$(CH_2)_n$Br, Cl, F or I       n = -0–6 or
$X_2$ is —$(CH_2)_n NH_2$       n = 0–6 or
$X_3$ is —NH—$(CH_2)_m$—$NH_2$       m = 2–6 or
$X_4$ is —NH—$(CH_2)_3$—NH—$(CH_2)_4$—$NH_2$ or
$X_5$ is —NH—$(CH_2)_3$—NH—$(CH_2)_4$—NH$(CH_2)_3$—$NH_2$
$X_6$ is

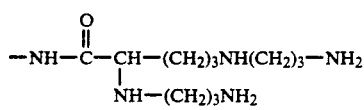

$X_7$ is

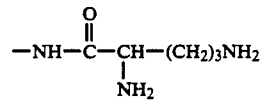

$X_8$ is

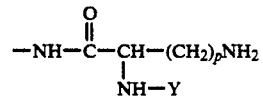

where
p is 2-5, Y is H or other groups attached by amide or alkyl amino group or
$X_9$ is a polyamine, e.g., polylysine, polyarginine, polybrene, histone or protamine or
$X_{10}$ is a reporter molecule, e.g.

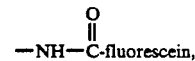

biotin, folic acid or PPD, or
$X_{11}$ is a polysaccharide or substituted polysaccharide, or
$X_{12}$ is a protein or
$X_{13}$ is an antibody or
$X_{14}$ is an amine or halide reactive group or
$X_{15}$ is —$(CH_2)_r$—SH where r is 0-6 or
$X_{16}$ is —$(CH_2)_x$—S—S—$(CH_2)_t$—$NH_2$ where s is 0-6 and t is 2-6.

Compounds of the invention are useful, either alone or in combination with other lipid aggregate-forming components, e.g., DOPE or cholesterol, for formulation into liposomes or other lipid aggregates. Such aggregates are cationic, able to complex with anionic macromolecules, such as nucleic acids. The lipid aggregate macromolecular complex interacts with cells making the macromolecule available for absorption and uptake by the cell. The halogenated compounds of the invention are also especially useful as intermediates for chemically coupling the cationic lipid to reporter molecules, proteins, polypeptides, antibodies, polysaccharides and the like to permit targeted delivery, quantitative assessment of targeting, greater efficiency of delivery and enhanced range of delivery capabilities.

Compounds of the invention can conjugate to a variety of useful molecules and substances such as polyamines, polyamine acids, polypeptides, proteins, fluorescent dyes, intercalating dyes, reporter molecules, biotin, polysaccharides, monosaccharides, solid support materials, magnetic beads, dendrimer particles, DEAE-Sephadex ™ (Pharmacia, Inc.), and the like. Depending on the specific compound of the invention and the substance to be conjugated thereto, conjugation can occur using a compound of the invention as an alkylating agent, using a free amine thereof to react with an amine-reactive group of the substance to be conjugated, or by the use of cross-linking agents.

BRIEF DESCRIPTION OF THE SCHEMES

Scheme 1 is a diagrammatic reaction scheme for synthesis of cationic lipids of the invention. Numerals identify the specific numbered compounds described in the Examples.

Scheme 2 is a diagrammatic reaction scheme for conjugating a halogenated compound of the invention ($X=X_1$) to molecules having an amino functionality (W).

Scheme 3 is a diagrammatic reaction scheme for conjugating a compound of the invention (e.g., $X=X_2-X_8$) to a molecule or substance having an amine-reactive group ($W_2$).

Scheme 4 is a diagrammatic reaction scheme for conjugating a compound of the invention (e.g., $X=X_2-X_8$) to another molecule or substance by use of a cross-linking agent.

DETAILED DESCRIPTION OF THE INVENTION

The present invention provides novel cationic lipids of the DORI family, however, they provide unique properties and advantages not heretofore available to the liposome art. The compounds can be used alone or in combination with other compounds, for example, DOPE, to prepare liposomes and other lipid aggregates suitable for transfection or delivery of compounds other than DNA to target cells, either in vitro or in vivo.

Compounds of the invention having a halogen substituent (X is $X_1$) are additionally useful for synthesis of more complex cationic lipids having the halogen replaced by a desired compound. The convenience of the halogen as a useful leaving group makes such substitutions straightforward. Examples of useful substituents include, without limitation, reporter groups, proteins, peptides, antibodies, carbohydrates, polysaccharides, and the like. Reporter groups can be any readily analyzed or visualized molecule, including, without limitation, fluorescent tags (Fluorescein, rhodamine), luminescent tags (4-methoxy-4-(3-phosphatephenyl)-spiro[1,2-dioxetane-3,2'-adamantane] (PPD)) biotin, dyes, chelators, affinity probes, etc. Such reporters enable visualization and measurement of target cell-lipid aggregate interactions. Such reporters also provide a means for subsequently accessing targeted cells, by providing surface binding sites unique to targeted cells. In addition, certain drugs and therapeutic compounds can be substituted at the halogen site, by a metabolizable linkage, thereby enhancing efficiency of drug delivery. Also, DNA intercalating compounds can be substituted, providing further DNA binding and enhancing transfection efficiency.

Compounds of the invention having an amide linked carboxyspermine ($X=X_6$), lysine ($X=X_8$) and shorter diamino acids ($X=X_7$) are especially efficient DNA delivery compounds, and can be used to form lipid aggregates by themselves, without combination with DOPE or other liposome-forming compound.

Compounds of the invention having the cationic lipid component coupled to a carbohydrate or polysaccharide ($X=X_{11}$), a polypeptide or protein ($X=X_{12}$) or an antibody ($X=X_{13}$) are useful in applications where the function of the substituent group is important. For example, specific delivery to a selected target cell type can be facilitated by a cationic lipid of the invention having a substituent that binds an antigen or receptor specific to the desired target cell. The ability to address a selected target cell type is especially useful in in vivo applications, for example in gene therapy.

DEFINITIONS

Lipid Aggregate is a generic term which includes liposomes of all types both unilamellar and multilamellar as well as micelles and more amorphous aggregates of cationic lipid or lipid mixed with amphipathic lipids such as phospholipids.

Target Cell refers to any cell to which a desired compound is delivered, using a lipid aggregate as carrier for the desired compound.

Transfection is used herein to mean the delivery of expressible nucleic acid to a target cell, such that the target cell is rendered capable of expressing said nucleic acid. It will be understood that the term "nucleic acid" includes both EDNA and RNA without regard to molecular weight, and the term "expression" means any manifestation of the functional presence of the nucleic acid within the cell, including without limitation, both transient expression and stable expression.

Delivery is used to denote a process by which a desired compound is transferred to a target cell such that the desired compound is ultimately located inside the target cell or in, or on the target cell membrane. In many uses of the compounds of the invention, the desired compound is not readily taken up by the target cell and delivery via lipid aggregates is a means for getting the desired compound into the cell. In certain uses, especially under in vivo conditions, delivery to a specific target cell type is preferable and can be facilitated by compounds of the invention.

The cationic lipids were prepared by following the general reaction scheme given below (Scheme 1).

3-dimethylamino-1,2-propanediol was treated with an alkali base followed with an alkylating agent of the desired length to obtain the corresponding dialkoxy derivative. To obtain the acyl derivatives the diol was treated with the desired acyl chloride in pyridine. Thus compound 1 was obtained by treating 3-dimethylamino-1,2-propanediol with oleyl mesylate in the presence of KOH in refluxing xylene.

Compound 1 was further alkylated using dibromoethane at high temperature to give compound 3. Treatment of compound 3 with diaminopropane or spermine at high temperature yielded compound 4 or compound 5, respectively.

Alkylation of compound 1 at 130° C. with 2-bromoethyl phthalimide yielded compound 7. Removal of the phthalimido group with hydrazine yielded compound 2. Compound 2 was acylated with tetra-t-butoxycarbonylspermine-carboxylic acid in the presence of dicyclohexylcarbodiimide to obtain compound 6. Removal of the BOC protecting group of compound 6 with trifluoroacetic acid resulted in compound 8.

The scheme provides a general method for the conjugation of lipids to any molecule or substance of interest. The alkylbromide 3 can be used as a general alkylating agent. Thus, any molecule of interest that has a nucleophilic moiety can react with compound 3 (Scheme 2) (J. March (1985) *Advanced Organic Chemistry*, John Wiley & Sons New York, pp. 364–366; Hilgetag & A. Martini eds (1972) *Preparative Organic Chemistry*, John Wiley & Sons, New York, pp. 448–460). For example, the primary amino group of polylysine reacts with the bromide to give polylysinelipid-conjugate. Other macromolecules that contain amino groups such as proteins and antibodies can also be conjugated to lipids in this manner. Smaller molecules that contain amino groups such as intercalators (methidium spermine), fluorescent dyes, nucleotides, nucleosides, amino acids, peptides and other reporter molecules such as biotin can also be conjugated in this manner.

Conversely, compounds 2, 4, 5, or 8 can be used for the conjugation of any molecules of interest that have electrophilic or nucleophilic sites. Compounds 2, 4, 5, or 8 can react with reporter molecules or other desired molecules if these molecules contain carboxylic acid sites, NHS ester or other active groups such as isothiocyanates, alkylhalides or chlorotriazines (Scheme 3) (Keezer, F. and Douraghi-Zdeh, K. (1967) Chem. Rev. 67:107; Dottario-Martin, B. and Ravel, J. H. (1978) Anal. Biochem. 76:562; Staros, J. V. (1982) Biochemistry 21:3950.

Compounds 2, 4, 5, or 8 can also be conjugated with molecules that contain nucleophilic sites such as amines by using cross-linking agents (Scheme 4). Disuccinimidyl suberate can be used to conjugate compounds 2, 4, 5, or 8 to molecules that contain an amino group (Staros, J. V. (1982) Biochemistry 21:3990). Cross-linking agents that contain NHS ester and maleimide can be used to conjugate compounds 2, 4, 5, or 8 to molecules that contain sulfhydryl group (Scheme 4) (Ji, T. H. (1979) Biochem. Biophys. Acta 559:39).

The compounds of the invention can be used in the same manner as are prior art compounds such as DOTMA, DOTAP, DOGS and the like. Methods for incorporating such cationic lipids into lipid aggregates are well-known in the art. Representative methods are disclosed by Felgner et al., supra; Eppstein et al. supra; Behr et al. supra; Bangham, A. et al. (1965) M. Mol. Biol. 23:238-252; Olson, F. et al. (1979) Biochim. Biophys. Acta 557:9-23; Szoka, F. et al. (1978) Proc. Natl. Acad. Sci. USA 75:4194-4198; Mayhew, E. et al. (1984) Biochim. Biophys. Acta 775:169-175; Kim, S. et al. (1983) Biochim. Biophys. Acta 728:339-348; and Fukunaga, M. et al. (1984) Endocrinol. 115:757-761. Commonly used techniques for preparing lipid aggregates of appropriate size for use as delivery vehicles include sonication and freeze-thaw plus extrusion. See, e.g., Mayer, L. et al. (1986) Biochim. Biophys. Acta 858:161-168. Microfluidization is used when consistently small (50-200 nm) and relatively uniform aggregates are desired (Mayhew, E., supra). Aggregates ranging from about 50 nm to about 200 nm diameter are preferred; however, both larger and smaller sized aggregates are functional.

Methods of transfection and delivery of other compounds are well-known in the art. The compounds of the present invention yield lipid aggregates that can be used in the same processes as those prior art compounds.

A one-to-one mixture (by weight) of the desired lipid and dioleylphosphatidyl ethanolamine was prepared in $CHCl_3$. The $CHCl_3$ was removed on the rotary evaporator to obtain a thin film of lipid mixture. The mixture was hydrated with enough water to obtain approximately 1.25 mg of lipid per ml of solution. The solution was passed through a microfluidizer twice and diluted to 1 mg/ml. The liposome formulation was then filtered through a 0.2 µ filter. Compound 8 was also formulated without DOPE either by sonication at 1 mg/ml in water or by dissolving a dried lipid film with ethanol and then adding water to give a final concentration of 2.5 mg/ml. Ethanol was 10% of that volume. In some instances, this was further diluted with water to 1 mg/ml, 4% ethanol.

The use of representative compounds of the invention is further detailed by reference to the following Examples. in each case, the ability of various compounds of the invention to provide efficient transfection was compared with a control using Lipofectin TM reagent. All abbreviations used herein are standard abbreviations in the art. Specific procedures not described in detail are either referenced or well-known in the art.

EXAMPLES

Example 1

2,3-dioleyloxy-1-(N,N-dimethylamino)propane (1).

To a three-necked, 2-liter round bottom flask equipped with a Dean-Stork trap were added 3-dimethylamino-1,2-propanediol (6.08 g, 51.1 mmoles), xylene (1300 ml) and KOH (8.0 g). The solution was refluxed for 2 hours while removing water azeotropically via the Dean-Stork trap. Oleyl mesylate (40.0 g, 115.6 mmoles) in 100 ml xylene was added to the reaction mixture drop-wise in 30 minutes. Refluxing was continued for 3 hours and the reaction mixture concentrated to a gum. The gum was triturated with 400 ml hexane and filtered. The solid was washed with 100 ml hexane followed with 200 ml ethyl acetate. The filtrates were combined, concentrated and subjected to flash chromatography. 2,3-dioleyloxy-1-(N,N-dimethylamino) propane was obtained as a colorless oil in 76% yield, TLC: $R_f=0.37$ (Silica gel: 5% EtOAc: hexane); IR: 2925, 2850, 1469, 1120, 1040 $cm^{-1}$; HNMR ($CDCl_3$) δ 5.35 (t, 4H), 4.13 (q, 1H) 3.4-3.65 (m, 6H), 2.35-2.45 (m, 2H), 2.25 (S, 6H), 1.95-2.05 (m, 8H), 1.5-1.65 (m, 4H), 1.2-1.45 (m, 4H) 0.9 (t, 6H).

Example 2

2H-Isoindole-2-ethanaminium, N-[2,3-bis(9-octadecenyloxy)-propyl]-1,3-dihydro-N,N-dimethyl-1,3-dioxo-, bromide (7).

2,3-dioleyloxy-1-(N,N-dimethylamino)propane (1.238 g, 2 mmole) was combined with N-(2-bromoethyl)phthalimide and heated under argon (130° C.) for 18 hours. TLC analysis (Silica gel 20% MeOH/$CHCl_3$) showed the lipid starting material was completely consumed. The desired material was purified by flash chromatography using step gradient of hexane/$CHCl_3$ (1:1), to 20% MeOH/$CHCl_3$. The desired material was obtained in 25% yield as a gum. IR: 2920, 2850, 1760(s), 1720, 1460, 1390 $cm^{-1}$.

Example 3

1-Propanaminium, N-(2-amino)ethyl-N,N-dimethyl-2,3-bis(9-octadecenyloxy)-bromide (2).

Compound 7 (800 mg) was combined with hydrazine (200 µl) in MeOH (30 ml). The reaction mixture was refluxed under argon for 20 hours. The reaction mixture was cooled and the precipitate was filtered off. The filtrate was concentrated to dryness. The desired product was obtained after reverse phase chromatography (C-18, 20% aqueous methanol) in 48% yield. IR: 3300, 2920, 2850, 1460 $cm^{-1}$.

Example 4

3-Oxa-5,9,15-triazaheptadecan-17-aminium, N-[2,3-bis(9-octadecenyloxy)propyl]-9-[(1,1-dimethylethoxy)-carbonyl]-13-{[(1,1-dimethylethoxy(carbonyl][3-{[(1,1-dimethylethoxy) -carbonyl]amino}propyl]amino}-N,N,2,2-tetramethyl-4,14-dioxo-, bromide (6). N,N,N,N-tetra-t-butoxy-5-spermine carboxylic acid (470 mg, 0.7 Moles) was treated with dicyclohexylcarbodiimide (206 mg, 1 Mole) and N-hydroxy succinimide (115 mg, 1 mmole) in 50 ml of 1:1 dioxane:$CH_2Cl_2$. The reaction mixture was stirred at room temperature overnight under argon. The dicyclohexyl urea that precipitated was filtered off. Compound 2 (220 mg) was dissolved in $CH_2Cl_2$ (10 ml) that contained triethylamine (24 μl) and added to the reaction mixture. The mixture was stirred at room temperature overnight. The solution was concentrated to dryness and taken in 100 ml $CHCl_3$ and extracted with 0.1 M $NaHCO_3$ (2×100 ml) followed with $H_2O$ (100 ml). The $CHCl_3$ layer was dried over $Na_2SO_4$ and concentrated. The desired material was obtained in 53% yield after flash chromatography. Rf=0.8 (20% MeOH in $CHCl_3$) IR: 2920, 2850, 1680, 1375, 1175 $cm^{-1}$.

Example 5

1-Propanaminium, N-[2-[[2,5-bis[(3-amino]-1-oxopentyl]amino]ethyl]-n,n-dimethyl-2,3,-bis(9-octadecenyloxy)-, tetra(trifluoroacetate) salt (8).

A solution of compound 6 in $CH_2Cl_2$ (160 mg in 2 ml) was treated with 2 ml of trifluoroacetic, acid/$CH_2Cl_2$ (1:1) at room temperature for 15 minutes. The mixture was then concentrated to dryness and co-evaporated with methanol (3×30 ml). The desired product was obtained in 68% yield after reverse phase chromatography (C-18, 20% aqueous methanol eluent). IR: 1920, 2850, 1680, 1210, 1140, $cm^{-1}$.

Example 6

1-Propanaminium, N-[2-(2-bromo)ethyl]-N,N-dimethyl-2,3-bis(9-octadecenyloxy)-,bromide (3). 2,3-dioleyloxy-1-(N,N-dimethylamino)propane (1.8 g) was dissolved in 9 ml of dibromoethane (that was passed through an alumina (III) column). The solution was heated at 80° C. for 8 hours and concentrated in vacuo to a gum. The gum was dissolved in minimum amount (~60 ml) hot $CH_3CN$ and cooled to −20° C. overnight. The yellowish precipitate was separated by decantation. The precipitate was dissolved in $CH_2Cl_2$ (120 ml) and decoionized with neutral norite. The $CH_2Cl_2$ was evaporated and the residue was crystallized from $CH_3CN$ as above to obtain the desired material in 43% yield.

Example 7

1-Propanaminium,N-{2-[[3-[[4-[(3-aminopropyl)amino]butyl]-amino]propyl]amino]ethyl}-n,n-dimethyl-2,3-bis-(9-octadecenyloxy)-, bromide (5).

Compound 3 (1.2 g) was treated with 3 ml of spermine at 80° C. for 2 days under argon. The reaction mixture was concentrated under vacuum at high temperature (50° C.). The mixture was co-evaporated with water (50 ml) followed with ethanol (50 ml) and used in transfection without further purification.

Example 8

1-Propanaminium, N-[2-[(3-aminopropyl)amino]ethyl]-N,N-dimethyl-2,3 -bis(9-octadecenyloxy)-, bromide (4).

Compound 3 (460 mg) was heated at 60° C. in 3 ml diaminopropane under Argon for 3 hours. The mixture was concentrated to dryness at 50° C. under vacuum. The gummy material that was obtained was co-evaporated with water (50 ml) followed with ethanol (50 ml). The material was used in transfection without further purification.

Example 9

Cell culture and plasmids.

Baby hamster kidney (BHK-21), COS-7, HeLa-S3 cells, and normal human fibroblasts isolated from newborn foreskin dermis were grown in Dulbecco's-modified Eagle's medium (DMEM) containing 10% fetal bovine serum (FBS), 2 mM L-glutamine (gln), 0.1 mM MEM nonessential amino acids (NEAA), 100 U/ml penicillin, and 100 μg/ml streptomycin. NIH-3T3 cells were grown in DMEM containing 10% calf serum (CS), 2 mMgln, 0.1 mM NEAA 100 U/ml penicillin, and 100 μg/ml streptomycin. PC12 cells were grown in DMEMcontaining 10% horse serum, 5% FBS, 2 mM gln, 0 1 mMNEAA, 100 U/ml penicillin and 100 μ/ml streptomycin. Jurkat cells (human lymphoid cell line) were grown in RPMI-1640 supplemented with 10% FBS, 2mML-glutamine, 100 U/ml penicillin, and 100 μg/ml streptomycin. Human keratinocytes were isolated from newborn foreskin epidermis and cultured in Keratinocyte Growth Medium (Clonetics, San Diego, Ca.). All cell lines were maintained in a humidified incubator with a 5% $CO_2$ atmosphere at 37° C.

pSV2CAT (5.0 Kb) was described previously (Gorman, C. M. et al. (1982) Mol. Cell. Biol. 2:1044). pCMVCAT (5.0 Kb) was also described previously (Foecking M. K. and Hofstetter, H. (1986) Gene 45:101). Plasmid DNA was purified by isopycnic centrifugation in CsCl/EtBr gradients after recovery by alkaline lysis (Maniatis, T. et al. (1982) in *Molecular Cloning: A Laboratory Manual*, Cold Spring Harbor Laboratory, Cold Spring Harbor, N.Y., pp. 90–91).

Example 10

Transient transfection of adherent cells (BHK-21, HeLa-S3, NIH-3T3. PC12. Cos-7. human keratinocytes, human fibroblasts) with cationic lipids.

For transient transfection of pSV2CAT DNA or pCMVCAT DNA, cells were plated in 6-well tissue culture dishes (35 mm wells) and incubated overnight to approximately 60% confluency. To transfect cells in one well, 1–2 μg of pSV2CAT DNA or pCMVCAT DNA was diluted in 100 μl Opti-MEM I. Cationic lipids were diluted separately in another 100 μl aliquot of Opti-MEM I. The two solutions were then mixed in a polystyrene tube, incubated for 10–15 min at room temperature to allow the formation of a DNA-liposome complex, and diluted to one ml by adding 0.8 ml Opti-MEM I or DMEM containing 5% fetal bovine serum (FBS), 2 mMgln, 0.1 mMNEAA, and lacking antibiotics. The cells were washed once with Opti-MEM I or serum-free DMEM, and the DNA-liposome complex was added directly to the cells. After a six hr incubation at 37° C., the transfection complexes were removed and two ml of DMEM containing 10% FBS, 2 mMgln, 0.2 mMNEAA, 100 U/ml penicillin, and 100 μg/ml streptomycin, was added to each well. Note: human keratinocytes were cultured and transfected in Keratinocyte Growth Medium. Cells were incubated for an additional 48 hrs and lysed in situ by freeze-thawing once or twice in 300 μl 0.1M Tris-HC1, pH 7.8–8.0 containing 0 1% Triton X-100. Cell lysates were assayed for CAT activity.

Example 11

Transient Transfection of Jurkat Cells with Cationic Lipids.

For transient nuclear expression of pSV2CAT or pCMVCAT in Jurkat cells, cells were washed with Opti-MEM I or serum-free RPMI 1640 containing 2 mM gln and plated in six-well plates at a density of 3×10⁶ cells per well in 0.8 ml Opti-MEM I or RPMI 1640. For each transfection, 5 μg pSV2CAT DNA or 2 μg pCMVCAT DNA was diluted in 100 μl Opti-MEM I. Lipids were diluted separately in another 100 μl aliquot of Opti-MEMI. The two solutions were then mixed in a polystyrene tube and incubated for 10-15 min at room temperature. The DNA-liposome complex was added to the cell suspensions and incubated 6 hours at 37° C., after which 4 ml growth medium were added per well (RPMI-1640; 10% FBS). Phorbol myristate acetate (Sigma Chemical Co., St. Louis, Mo.) and phytohemagglutinin (Sigma) were also added to a final concentration of 50 ng/ml and 1 μg/ml, respectively, to activate the cells. Cells were harvested at approximately 48 hours post-transfection by centrifugation. Cell lysates were prepared by resuspending cell pellets at 0° C. in 0.1 M Tris-HCl pH 8.0 containing 0.1% Triton X-100 and freeze-thawing once. Cell lysates were cleared by centrifugation and assayed for CAT activity.

Example 12

Chloramphenicol acetyltransferase (CAT) assay.

Cell lysates were assayed for CAT activity as described by Neumann et al. (1987) BioTechniques 5:444 using [$^{14}$C]-butyryl coenzyme A (New England Nuclear, Boston, Mass.). The enzyme reactions were incubated for 2 hrs at 37° C., overlayed with 3.0 ml Econofluor (New England Nuclear) and then incubated for an additional 2 hrs to allow diffusion of the acetylated chloramphenicol into the scintillation fluid. CAT activity was determined by measuring radioactivity in a liquid scintillation counter.

Example 13

Results.

Results are shown in Tables 1-8. The "% protein" column indicates the relative amount of protein in the sample tested for CAT activity and therefore provides a way to estimate toxicity of the compounds being tested. The "CAT Activity" column indicates the relative transfection effectiveness of the lipid formulation in the various cell lines. The control sample was a cell culture grown under similar conditions as those that were transfected, but with no DNA or cationic lipid added. Protein was measured using a commercially available Bradford protein assay (BioRad Laboratories, Richmond, Ca.).

For BHK-21 (Table 1), NIH-3T3 (Table 2B), keratinocytes (Table 3), PC12 (Table 4), Jurkat (Table 5), and Cos-7 (Table 6) cells, compound 8 was highly effective for DNA transfection with minimal toxicity. Fibroblasts (Table 7) were also successfully transfected with compound 8. Compounds 4 and 5 were also effective for DNA transfection in keratinocytes (Table 3), and compound 3 had good activity in HeLa-S3 cells in the presence or absense of serum (Table 8). Compounds 2 and 3 also had good activity for DNA transfection in NIH-3T3 cells (Tables 2A and 2B).

TABLE 1

TRANSFECTION RESULTS WITH BHK-21 CELLS

| LIPID | CAT ACTIVITY (CPM) | μg LIPID | % protein (% of control) |
|---|---|---|---|
| COMPOUND 2/DOPE | 12202 | 3 μg | 57 |
| COMPOUND 3/DOPE | 11,226 | 6 μg | 29 |
| COMPOUND 8/DOPE | 73,628 | 6 μg | 83 |
| COMPOUND 8/DOPE | 49,417 | 18 μg | 103 |
| COMPOUND 8 (EtOH) | 67,858 | 3.8 μg | 59 |
| COMPOUND 8 | 73,856 | 6 μg | 114 |

TABLE 1-continued

TRANSFECTION RESULTS WITH BHK-21 CELLS

| LIPID | CAT ACTIVITY (CPM) | μg LIPID | % protein (% of control) |
|---|---|---|---|
| SONICATED | | | |

Transfections were for 6 hours in OPTI-MEM I with 1 μg pSV2CAT DNA, in 35 mm wells. 3 μl of 300 μl extract assayed for CAT activity.

TABLE 2A

NIH-3T3 (Mouse fibroblast cell line)

| LIPID | CAT ACTIVITY (CPM) | μg LIPID | % protein (% of control) |
|---|---|---|---|
| COMPOUND 4 | 3,114 | 24 μg | 111% |
| COMPOUND 5/DOPE | 1,180 | 26 μg | 92% |
| COMPOUND 3 | 6,074 | 16 μg | 35% |

Transfections for 6 hours in OPTI MEM serum-free medium with 2 μg pSV2CAT DNA.

TABLE 2B

NIH-3T3 (MOUSE FIBROBLAST CELL LINE)

| LIPID | CAT ACTIVITY (CPM/150 ul) | μg LIPID | % protein (% of control) |
|---|---|---|---|
| COMPOUND 8/DOPE | 17,564 | 12 μg | 100% |
| COMPOUND 8 | 30,488 | 15 μg | 89% |
| COMPOUND 2/DOPE | 14,890 | 12 μg | 68% |
| COMPOUND 3/DOPE | 13,002 | 18 μg | 55% |
| COMPOUND 4/DOPE | 1,446 | 18 μg | 104% |

DNA-Lipid complexes made in OPTI-MEM. Transfections for 6 hours in DMEM with 2 μg pCMVCAT DNA.

TABLE 3

NORMAL HUMAN KERATINOCYTES

| LIPID | CAT ACTIVITY (CPM) | μg LIPID | % protein (% of control) |
|---|---|---|---|
| COMPOUND 4 | 20,038 | 40 μg | 41% |
| COMPOUND 5/DOPE | 17,818 | 90 μg | 39% |
| COMPOUND 3 | 10,598 | 10 μg | 42% |
| COMPOUND 8 (EtoH) | 33,818 | 25 μg | 38% |
| COMPOUND 8/DOPE | 20,410 | 25 μg | 65% |

Transfections for 5 hours (compound 8) or 6 hours (compounds 3, 4, and 5) with 2 μg pSV2CAT DNA in 35 mm well. 50 μl of 300 μl assayed for CAT activity.

TABLE 4

TRANSFECTION RESULTS WITH PC12 CELLS (RAT PHEOCHROMOCYTOMA CELL LINE)

| LIPID | CAT ACTIVITY (CPM/150 ul) | μg LIPID | % protein (% of control) |
|---|---|---|---|
| COMPOUND 8/DOPE | 12,950 | 15 μg | 87% |
| COMPOUND 8 | 28,512 | 40 μg | 66% |

DNA-lipid complexes were made in OPTI-MEM. PC12 cells (6 × 10$^5$ cells) were transfected in DMEM with 2 μg of pCMVCAT DNA for 6 hours.

TABLE 5A

TRANSFECTION RESULTS WITH JURKAT CELLS (HUMAN T-LYMPHOMA CELL LINE) WITH pSV2CAT

| LIPID | CAT ACTIVITY (CPM/150 μl) | μg LIPID | % protein (% of control) |
|---|---|---|---|
| COMPOUND 4 | 2252 | 20 μg | 93% |
| COMPOUND 5 | 1170 | 20 μg | 100% |
| COMPOUND 4 | 820 | 30 μg | 100% |
| COMPOUND 5/DOPE | 702 | 30 μg | 76% |

TABLE 5A-continued
TRANSFECTION RESULTS WITH JURKAT CELLS (HUMAN T-LYMPHOMA CELL LINE) WITH pSV2CAT

| LIPID | CAT ACTIVITY (CPM/150 μl) | μg LIPID | % protein (% of control) |
|---|---|---|---|
| COMPOUND 3 | 3008 | 30 μg | 97% |

Jurkat cells (3 × 10⁶ cells) were transfected in OPTI-MEM with 5 μg of pSV2CAT DNA for 6 hours.

TABLE 5B
TRANSFECTION RESULTS WITH JURKAT CELLS (HUMAN T-LYMPHOMA CELL LINE) WITH pCMVCAT

| LIPID | CAT ACTIVITY (CPM/150 ul) | μg LIPID | % protein (% of control) |
|---|---|---|---|
| COMPOUND 8/DOPE | 12,766 | 30 μg | 113% |
| COMPOUND 8 | 44,996 | 15 μg | 47% |

DNA-lipid complexes were made in OPTI-MEM. Jurkat cells (3 × 10⁶ cells) were transfected in RPMI-1640 with 2 μg of pCMVCAT DNA for 6 hours.

TABLE 6
COS-7 CELLS

| LIPID | CAT ACTIVITY (CPM/150 ul) | μg LIPID | % protein (% of control) |
|---|---|---|---|
| COMPOUND 8 | 14,282 | 12 μg | 99.1% |

TABLE 6-continued
COS-7 CELLS

| LIPID | CAT ACTIVITY (CPM/150 ul) | μg LIPID | % protein (% of control) |
|---|---|---|---|
| COMPOUND 8 DOPE | 53,875 | 6 μg | 68.9% |

DNA-lipid complexes were made in DMEM. Cos-7 cells (1 × 10⁵ cells) were transfected in DMEM with 1 μg of pSV2CAT DNA for 6 hours.

TABLE 7
TRANSFECTION RESULTS WITH NORMAL HUMAN FIBROBLASTS

| LIPID | CAT ACTIVITY (CPM) | μg LIPID | % protein (% of control) |
|---|---|---|---|
| COMPOUND 8 (EtOH) | 4,288 | 6 μg | 56 |
| COMPOUND 8/DOPE | 11,486 | 18 μG | 18 |

Transfection for 6 hours in OptiMEM I with 2μ pSV2CAT DNA. 150 μl of 300 μl extract assayed for CAT activity.

TABLE 8
TRANSFECTION OF HeLa-S3 CELLS BY COMPOUND 3

| MEDIUM | CAT ACTIVITY (CPM) | μg LIPID | % protein (% of control) |
|---|---|---|---|
| DMEM, 5% FBS | 78,798 | 6 μg | 54% |
| OPTIMEM I, 0% FBS | 29,400 | 12 μg | 43% |

Transfections for 6 hours with 2 μg pSV2CAT DNA.

SCHEME 1

$R = -(CH_2)_8-CH=CH-(CH_2)_7CH_3$ 5,334,761
-continued
SCHEME 1
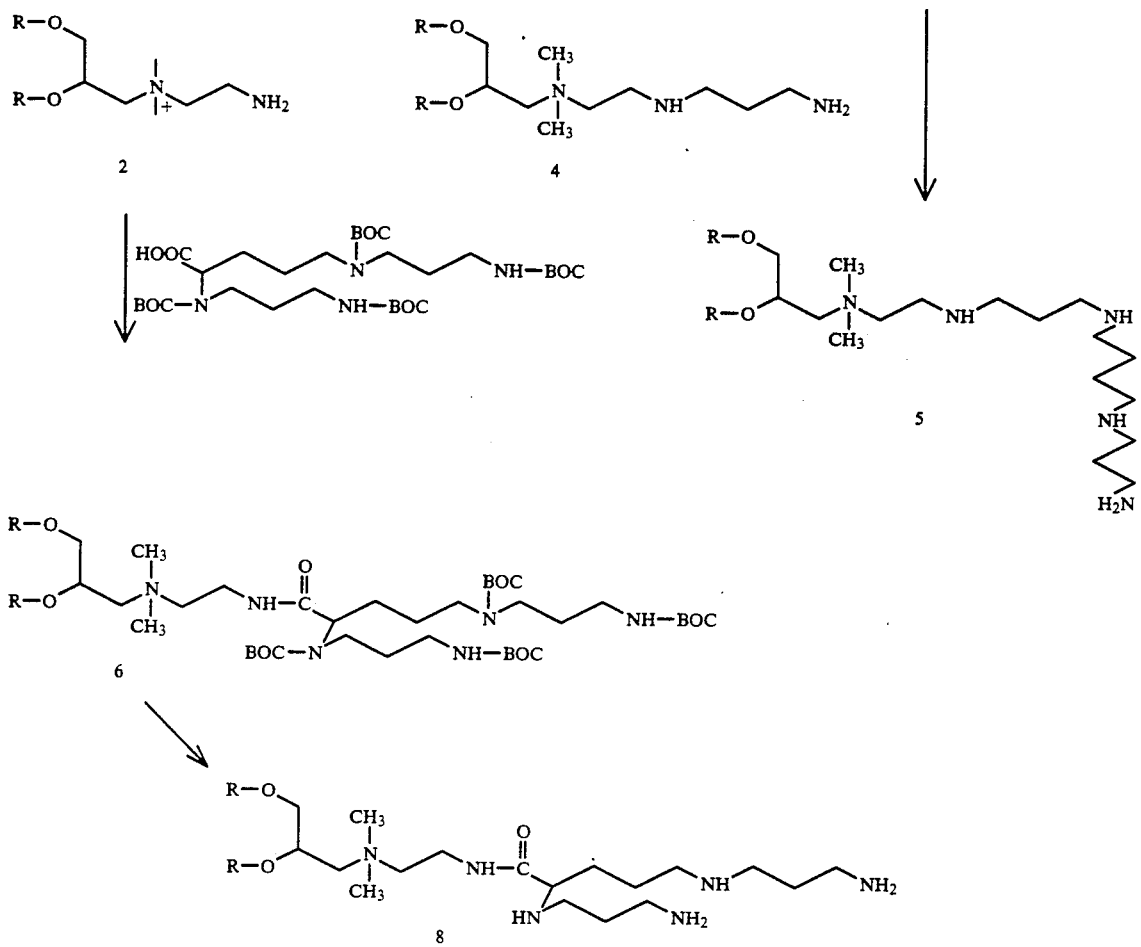
SCHEME 2
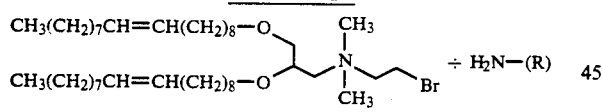
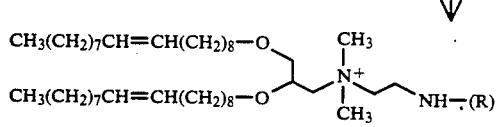
R = POLYLYSINE
POLYAMINE ACID
POLYPEPTIDE
PROTEIN
FLUORESCENT DYES
INTERCALATORS
REPORTER MOLECULES
POLYAMINE
SCHEME 3
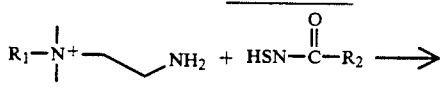
-continued
SCHEME 3
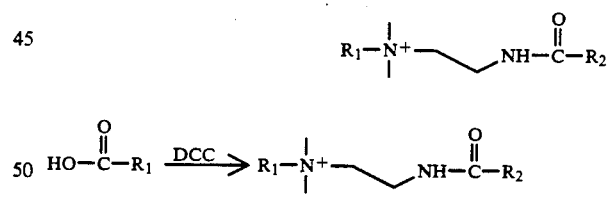
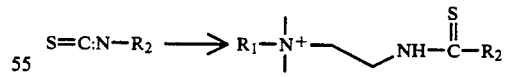
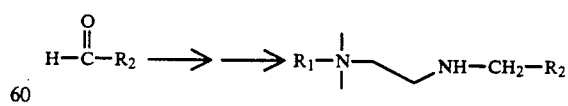
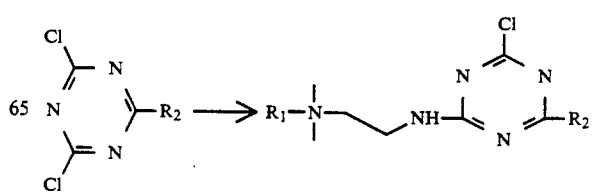

-continued
SCHEME 3

R2 = FLUORESCENT DYES
 INTERCALATORS
 REPORTER MOLECULES
 BIOTIN
 POLYSACCHARIDES
 MONOSACCHARIDES
 SOLID SUPPORT
 MAGNETIC BEADS

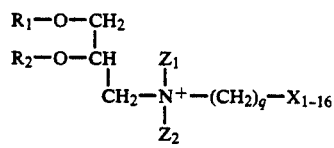

wherein $R_1$ and $R_2$ independently of another, are $C_{1-23}$ alkyl or alkenyl, or

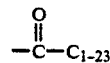

SCHEME 4

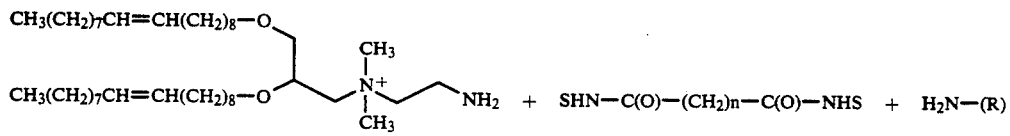

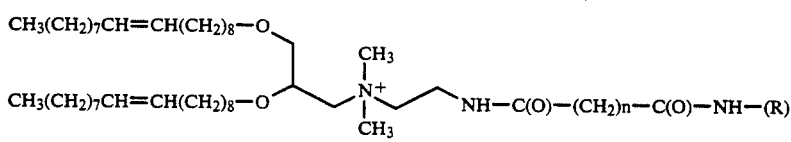

R = POLYLYSINE
 POLYAMINE ACID
 POLYPEPTIDE
 PROTEIN
 FLUORESCENT DYES
 INTERCALATERS
 REPORTER MOLECULES
 POLYAMINE

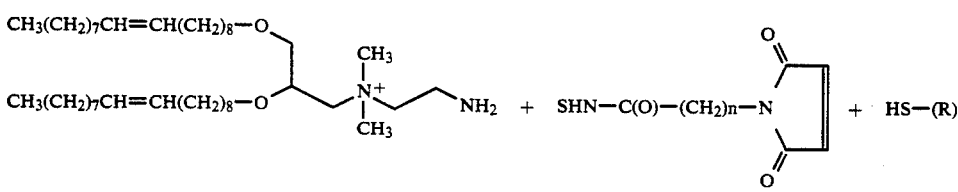

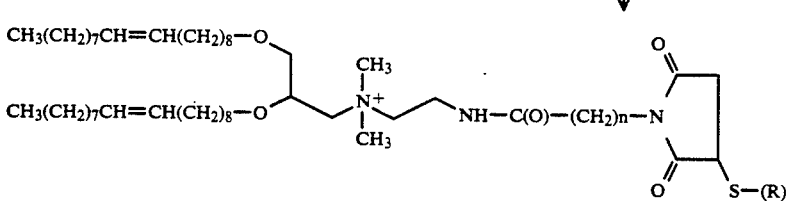

R = POLYPEPTIDE
 PROTEIN
 FLUORESCENT DYES
 INTERCALATORS
 REPORTER MOLECULES

We claim:
1. A composition having the structure alkyl or alkenyl,
$Z_1$ and $Z_2$ independently of one another, are H or unbranched alkyl $C_{1-6}$, q is 1 to 6,
X is selected from any of $X_1$-$X_8$, $X_{15}$ and $X_{16}$ where $X_1$ is $-(CH_2)_nBr$, $(CH_2)_nCl$, $(CH_2)_nF$, $(CH_2)_nF$ or $(CH_2)_nI$ where $n=0-6$ or $X_2$ is $-(CH_2)_nNH_2$    $n=0-6$ or $X_3$ is $-NH-(CH_2)_m-NH_2$    $m=2-6$ or $X_4$ is $-NH-(CH_2)_3-NH-(CH_2)_4-NH_2$ or $X_5$ is $-NH-(CH_2)_3-NH-(CH_2)_4-NH(CH_2)_3-NH_2$ or $X_6$ is

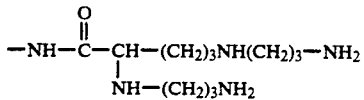

$X_7$ is

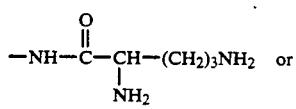

$X_8$ is

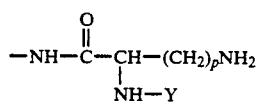

$X_{15}$ is $-(CH_2)_r-SH$ where r is 0-6 or $X_{16}$ is $-(CH_2)_s-S-S-(CH_2)_t-NH_2$ where s is 0-6 and t is 2-6.

2. A compound according to claim 1 wherein X is $X_2$.

3. A compound according to claim 1 wherein X is $X_2$, and n is 2.

4. A compound according to claim 1 wherein X is $X_2$, n is 1, $R_1=R_2$ is $C_{18}$ alkenyl and $Z_1=Z_2$ is methyl.

5. A compound according to claim 1 wherein X is $X_1$.

6. A compound according to claim 1 wherein X is $X_1$ is $(CH_2)_nBr$ where n is 1.

7. A compound according to claim 1 wherein X is $X_1$ is $(CH_2)_nBr$ where n is 1, $R_1=R_2$ is $C_{18}$ alkenyl and $Z_1=Z_2$ is methyl.

8. A compound according to claim 1 wherein X is $X_3$.

9. A compound according to claim 1 wherein X is $X_3$, q is 2, and m is 3.

10. A compound according to claim 1 wherein X is $X_3$, q is 2, m is 3, $Z_1=Z_2$ is methyl and $R_1=R_2$ is $C_{18}$ alkenyl.

11. A compound according to claim 1 wherein X is $X_5$.

12. A compound according to claim 1 wherein X is $X_5$ and q is 2.

13. A compound according to claim 1 wherein X is $X_5$, q is 2, $Z_1=Z_2$ is methyl, and $R_1=R_2$ is $C_{18}$ alkenyl.

14. A compound according to claim 1 wherein X is $X_6$.

15. A compound according to claim 1 wherein X is $X_6$ and q is 2.

16. A compound according to claim 1 wherein X is $X_6$, q is 2, $Z_1=Z_2$ is methyl and $R_1=R_2$ is $C_{18}$ alkenyl.

17. A lipid aggregate comprising a compound of claim 1.

18. A kit for preparing a lipid aggregate comprising a cationic lipid according to claim 1.

* * * * *

UNITED STATES PATENT AND TRADEMARK OFFICE
CERTIFICATE OF CORRECTION

PATENT NO. : 5,334,761

DATED : August 2, 1994

INVENTOR(S) : Gebeyehu et al.

It is certified that error appears in the above-indentified patent and that said Letters Patent is hereby corrected as shown below:

Delete the structure bridging columns 1 and 2 and replace with:

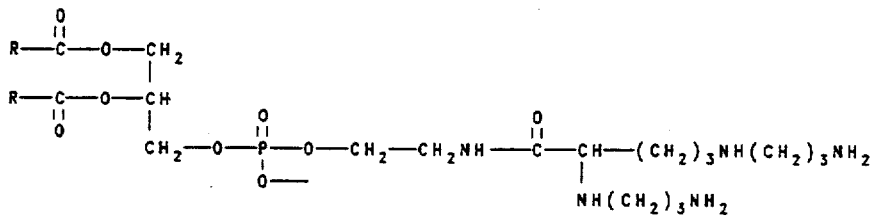

In columns 13 and 14, delete the division sign, "÷", which appears in Scheme 1 and replace with a plus sign, --+--.

In columns 15 and 16, delete the division sign, "÷", which appears in Scheme 2 and replace with a plus sign, --+--.

Delete the structure at the top of column 18 and replace with:

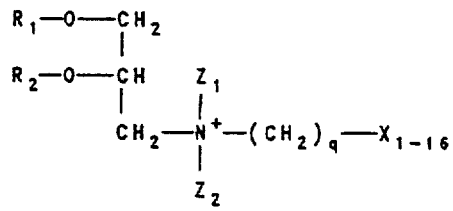

In column 19, line 1, delete "$(CH_2)_nF$,".

UNITED STATES PATENT AND TRADEMARK OFFICE
CERTIFICATE OF CORRECTION

PATENT NO. : 5,334,761
DATED : August 2, 1994
INVENTOR(S) : Gebeyehu et al.

It is certified that error appears in the above-indentified patent and that said Letters Patent is hereby corrected as shown below:

In column 19, at line 29, insert --where p is 2-5, y is H or-- on the line above and preceding "$X_{15}$ is".

Signed and Sealed this

Second Day of May, 1995

Attest:

BRUCE LEHMAN

Attesting Officer

Commissioner of Patents and Trademarks